United States Patent
Xue et al.

(10) Patent No.: US 11,987,826 B2
(45) Date of Patent: May 21, 2024

(54) NITRILASE MUTANT AND APPLICATION THEREOF IN THE SYNTHESIS OF AN ANTI-EPILEPTIC DRUG INTERMEDIATE

(71) Applicant: ZHEJIANG UNIVERSITY OF TECHNOLOGY, Zhejiang (CN)

(72) Inventors: Yaping Xue, Zhejiang (CN); Neng Xiong, Zhejiang (CN); Peijin Lv, Zhejiang (CN); Yuguo Zheng, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 17/604,623

(22) PCT Filed: Dec. 11, 2020

(86) PCT No.: PCT/CN2020/135583
§ 371 (c)(1),
(2) Date: Oct. 18, 2021

(87) PCT Pub. No.: WO2021/147558
PCT Pub. Date: Jul. 29, 2021

(65) Prior Publication Data
US 2022/0177868 A1    Jun. 9, 2022

(30) Foreign Application Priority Data
Jan. 21, 2020 (CN) .......................... 202010071083.9

(51) Int. Cl.
*C12N 9/78* (2006.01)
*C12P 7/40* (2006.01)
*C12P 7/54* (2006.01)
*C12P 13/00* (2006.01)

(52) U.S. Cl.
CPC .............. *C12N 9/78* (2013.01); *C12P 13/002* (2013.01); *C12Y 305/05001* (2013.01)

(58) Field of Classification Search
None
See application file for complete search history.

(56) References Cited

U.S. PATENT DOCUMENTS

2013/0288315 A1* 10/2013 Vogel ...................... C12P 7/42
435/227

FOREIGN PATENT DOCUMENTS

| CN | 101629192 A | 1/2010 |
|---|---|---|
| CN | 102796772 A | 11/2012 |
| CN | 102911975 A | 2/2013 |
| CN | 104212784 A | 12/2014 |
| CN | 105296512 A | 2/2016 |
| CN | 107177576 A | 9/2017 |
| CN | 108486088 A | 9/2018 |
| CN | 111172140 A | 5/2020 |

OTHER PUBLICATIONS

Kobayashi et al., "Nitrilase from Rhodococcus rhodochrous J1. Sequencing and overexpression of the gene and identification of an essential cysteine residue", J. Biol. Chem. 267:20746-20751, 1992 (Year: 1992).*
Singh et al., Curr. Protein Pept. Sci. 18:1-11, 2017 (Year: 2017).*
Zhang et al., Structure 26:1474-1485, 2018 (Year: 2018).*
UniProt Database Accession No. A0A1C3XDR2, Dec. 2017, 1 page (Year: 2017).*
Liu, Z.Q. et al., "Screening and Improving the Recombinant Nitrilases and Application in Biotransformation of Iminodiacetonitrile to Iminodiacetic Acid.", Plos One., vol. 8, No. 6, Jun. 27, 2013 (Jun. 27, 2013), chapter e67197, pp. 1-9 ; (pp. 9).

* cited by examiner

*Primary Examiner* — David Steadman
(74) *Attorney, Agent, or Firm* — Muncy, Geissler, Olds & Lowe, P.C.

(57) ABSTRACT

The present invention provides a nitrilase mutant protein with increased thermal stability and its application in the synthesis of an anti-epileptic drug intermediate, wherein the mutant is obtained by mutating one or two of the amino acids at position 151, 223 and 250 of the amino acid sequence shown in SEQ ID No. 2. the thermal stability of the nitrilase mutant AcN-T151V/C223A/C250G was increased by up to 1.73 folds. The yield of the final product was up to 95% using the recombinant *Escherichia coli* containing the nitrilase mutant to hydrolyze 1M 1-cyanocyclohexylacetonitrile to produce 1-cyanocyclohexyl acetic acid at 35° C. And the yield of the final product was up to 97% when hydrolyzing 1.2M 1-cyanocyclohexylacetonitrile at 35° C. The final yield was up to 80% when using the nitrilase mutants obtained by the present invention to synthesize gabapentin.

8 Claims, 5 Drawing Sheets
Specification includes a Sequence Listing.

SEQUENCE LISTING

```
<160> NUMBER OF SEQ ID NOS: 24

<210> SEQ ID NO 1
<211> LENGTH: 1134
<212> TYPE: DNA
<213> ORGANISM: Acidovorax facilis

<400> SEQUENCE: 1
atggtatctt acaactccaa atttctggct gctaccgtac aggctgaacc ggtttggctg      60
gacgcggacg caactatcga taatctatt ggtatcatcg aggaggcggc ccagaaaggt     120
gcgtctctga ttgccttccc ggaagttttc atccctggtt acccgtattg ggcctggctg     180
ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt tatcgacgaa     360
cgtggtgaaa tcgttgctaa ccgtcgtaaa ctgaaaccaa ctcacgttga acgtacgatt     420
tatggtgaag gcaacggtac cgactttctg acgcatgact tcgcatttgg tcgtgttggt     480
ggtctgaact gctgggagca cgttcagccg ctgtccaaat tcatgatgta ctccctgggt     540
gaacaggtac acgtcgcttc ttggccggct atgtcccgc tgcaaccgga cgtgtttcaa     600
ttttccatcg aggctaatgc gaccgtaacc cgctcctatg ctattgaagg ccaaaccttc     660
gttctgtgct ctacgcaggt tatcggtccg tctgcaattg aaaccttctg tctgaacgat     720
```

```
gagcaacgtg cactgctgcc gcagggttgc ggttgggcgc gtatctacgg cccggacggc      780
agcgaactgg ccaagccgct ggctgaagac gcagagggta ttctgtacgc agaaatcgat      840
ctggaacaga ttctgctggc caaggctggc gctgatccgg ttggtcacta cagccgccct      900
gatgtcctgt ccgtgcagtt cgacccgcgt aaccacaccc cggtacaccg cattggtatc      960
gatggccgtc tggatgttaa cacgcgttcc cgtgtagaaa actttcgcct gcgtaaagca     1020
gcagaaaaag aacgtcaggc cagcaaacgt ctgggcacga actgtttga acagtctctg     1080 ctggcggagg agccggtacc agccaaactc gagcaccacc accaccacca ctga           1134
```

<210> SEQ ID NO 2
<211> LENGTH: 377
<212> TYPE: PRT
<213> ORGANISM: Acidovorax facilis

<400> SEQUENCE: 2

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Phe Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300
```

```
Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
            325                 330                 335

Leu Arg Lys Ala Ala Glu Lys Glu Arg Gln Ala Ser Lys Arg Leu Gly
        340                 345                 350

Thr Lys Leu Phe Glu Gln Ser Leu Leu Ala Glu Glu Pro Val Pro Ala
    355                 360                 365

Lys Leu Glu His His His His His His
    370                 375

<210> SEQ ID NO 3
<211> LENGTH: 1134
<212> TYPE: DNA
<213> ORGANISM: Acidovorax facilis

<400> SEQUENCE: 3
atggtatctt acaactccaa atttctggct gctaccgtac aggctgaacc ggtttggctg    60
gacgcggacg caactatcga taaatctatt ggtatcatcg aggaggcggc ccagaaaggt   120
gcgtctctga ttgccttccc ggaagttttc atccctggtt accgtattg ggcctggctg    180 ggtgacgtaa agtactccct gtccttcacc tcccgttacc acgaaaactc cctggaactg   240
ggtgacgacc gtatgcgccg tctgcaactg gctgcgcgtc gtaacaaaat cgcgctggtt   300
atgggttaca gcgagcgtga ggcaggcagc cgctacctgt cccaggtctt tatcgacgaa   360
cgtggtgaaa tcgttgctaa ccgtcgtaaa ctgaaaccaa ctcacgttga acgtacgatt   420
tatggtgaag gcaacggtac cgactttctg gtgcatgact tcgcatttgg tcgtgttggt   480
ggtctgaact gctgggagca cgttcagccg ctgtccaaat tcatgatgta ctccctgggt   540
gaacaggtac acgtcgcttc ttggccggct atgtccccgc tgcaaccgga cgtgtttcaa   600
ttttccatcg aggctaatgc gaccgtaacc cgctcctatg ctattgaagg ccaaaccttc   660
gttctgtgct ctacgcaggt tatcggtccg tctgcaattg aaaccttctg tctgaacgat   720
gagcaacgtg cactgctgcc gcagggttgc ggttgggcgc gtatctacgg cccggacggc   780
agcgaactgg ccaagccgct ggctgaagac gcagagggta ttctgtacgc agaaatcgat   840
ctggaacaga ttctgctggc caaggctggc gctgatccgg ttggtcacta cagccgccct   900
gatgtcctgt ccgtgcagtt cgacccgcgt aaccacaccc cggtacaccg cattggtatc   960
gatggccgtc tggatgttaa cacgcgttcc cgtgtagaaa actttcgcct gcgtaaagca   1020
gcagaaaaag aacgtcaggc cagcaaacgt ctgggcacga actgtttga acagtctctg   1080 ctggcggagg agccggtacc agccaaactc gagcaccacc accaccacca ctga         1134

<210> SEQ ID NO 4
<211> LENGTH: 377
<212> TYPE: PRT
<213> ORGANISM: Acidovorax facilis

<400> SEQUENCE: 4

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45
```

```
Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
130                 135                 140

Asn Gly Thr Asp Phe Leu Val His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Phe Ser Ile Glu Ala Asn Ala Thr
            195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Lys Ala Ala Glu Lys Glu Arg Gln Ala Ser Lys Arg Leu Gly
            340                 345                 350

Thr Lys Leu Phe Glu Gln Ser Leu Leu Ala Glu Pro Val Pro Ala
            355                 360                 365

Lys Leu Glu His His His His His
    370                 375

<210> SEQ ID NO 5
<211> LENGTH: 1134
<212> TYPE: DNA
<213> ORGANISM: Acidovorax facilis

<400> SEQUENCE: 5
atggtatctt acaactccaa atttctggct gctaccgtac aggctgaacc ggtttggctg     60
gacgcggacg caactatcga taatctatt ggtatcatcg aggaggcggc ccagaaaggt    120
gcgtctctga ttgccttccc ggaagttttc atccctggtt accgtattg gcctggctg     180 ggtgacgtaa agtactccct gtccttcacc tcccgttacc acgaaaactc cctggaactg    240
```

```
ggtgacgacc gtatgcgccg tctgcaactg gctgcgcgtc gtaacaaaat cgcgctggtt      300
atgggttaca gcgagcgtga ggcaggcagc cgctacctgt cccaggtctt tatcgacgaa      360
cgtggtgaaa tcgttgctaa ccgtcgtaaa ctgaaaccaa ctcacgttga acgtacgatt      420
tatggtgaag caacggtac cgactttctg acgcatgact tcgcatttgg tcgtgttggt      480
ggtctgaact gctgggagca cgttcagccg ctgtccaaat tcatgatgta ctccctgggt      540
gaacaggtac acgtcgcttc ttggccggct atgtccccgc tgcaaccgga cgtgtttcaa      600
ttttccatcg aggctaatgc gaccgtaacc cgctcctatg ctattgaagg ccaaaccttc      660
gttctggcgt ctacgcaggt tatcggtccg tctgcaattg aaaccttctg tctgaacgat      720
gagcaacgtg cactgctgcc gcagggttgc ggttgggcgc gtatctacgg cccggacggc      780
agcgaactgg ccaagccgct ggctgaagac gcagagggta ttctgtacgc agaaatcgat      840
ctggaacaga ttctgctggc caaggctggc gctgatccgg ttggtcacta cagccgccct      900
gatgtcctgt ccgtgcagtt cgacccgcgt aaccacaccc cggtacaccg cattggtatc      960
gatggccgtc tggatgttaa cacgcgttcc cgtgtagaaa actttcgcct gcgtaaagca     1020
gcagaaaaag aacgtcaggc cagcaaacgt ctgggcacga aactgtttga acagtctctg     1080
ctggcggagg agccggtacc agccaaactc gagcaccacc accaccacca ctga           1134
```

<210> SEQ ID NO 6
<211> LENGTH: 377
<212> TYPE: PRT
<213> ORGANISM: Acidovorax facilis

<400> SEQUENCE: 6

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Phe Ser Ile Glu Ala Asn Ala Thr
        195                 200                 205

Val Thr Arg Ser Tyr Ala Ile Glu Gly Gln Thr Phe Val Leu Ala Ser
    210                 215                 220
```

```
Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
            245                 250                 255

Gly Pro Asp Gly Ser Glu Leu Ala Lys Pro Leu Ala Glu Asp Ala Glu
        260                 265                 270

Gly Ile Leu Tyr Ala Glu Ile Asp Leu Glu Gln Ile Leu Leu Ala Lys
    275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Lys Ala Ala Glu Lys Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys Leu Glu His His His His His
    370                 375

<210> SEQ ID NO 7
<211> LENGTH: 1134
<212> TYPE: DNA
<213> ORGANISM: Acidovorax facilis

<400> SEQUENCE: 7
atggtatctt acaactccaa atttctggct gctaccgtac aggctgaacc ggtttggctg      60
gacgcggacg caactatcga taatctatt ggtatcatcg aggaggcggc ccagaaaggt     120
gcgtctctga ttgccttccc ggaagttttc atccctggtt accgtattg gcctggctg      180 ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt atcgacgaa      360 cgtggtgaaa tcgttgctaa ccgtcgtaaa ctgaaaccaa ctcacgttga acgtacgatt     420
tatggtgaag caacggtac cgactttctg acgcatgact tcgcatttgg tcgtgttggt      480
ggtctgaact gctgggagca cgttcagccg ctgtccaaat tcatgatgta ctccctgggt     540
gaacaggtac acgtcgcttc ttggccggct atgtccccgc tgcaaccgga cgtgtttcaa     600
ttttccatcg aggctaatgc gaccgtaacc cgctcctatg ctattgaagg ccaaaccttc     660
gttctgtgct ctacgcaggt tatcggtccg tctgcaattg aaaccttctg tctgaacgat     720
gagcaacgtg cactgctgcc gcagggtggc ggttgggcgc gtatctacgg cccggacggc     780
agcgaactgg ccaagccgct ggctgaagac gcagagggta ttctgtacgc agaaatcgat     840
ctggaacaga ttctgctggc caaggctggc gctgatccgg ttggtcacta cagccgccct     900
gatgtcctgt ccgtgcagtt cgacccgcgt aaccacaccc cggtacaccg cattggtatc     960
gatggccgtc tggatgttaa cacgcgttcc cgtgtagaaa actttcgcct gcgtaaagca    1020
gcagaaaaag aacgtcaggc cagcaaacgt ctgggcacga actgtttga acagtctctg    1080 ctggcggagg agccggtacc agccaaactc gagcaccacc accaccacca ctga          1134

<210> SEQ ID NO 8
```

```
<211> LENGTH: 377
<212> TYPE: PRT
<213> ORGANISM: Acidovorax facilis

<400> SEQUENCE: 8
```

| | | | | | | | | | | | | | | |
|---|---|---|---|---|---|---|---|---|---|---|---|---|---|---|
|Met|Val|Ser|Tyr|Asn|Ser|Lys|Phe|Leu|Ala|Ala|Thr|Val|Gln|Ala|Glu|
|1| | | |5| | | | |10| | | | |15|

Met Val Ser Tyr Asn Ser Lys Phe Leu Ala Ala Thr Val Gln Ala Glu
1               5               10              15

Pro Val Trp Leu Asp Ala Asp Ala Thr Ile Asp Lys Ser Ile Gly Ile
                20              25              30

Ile Glu Glu Ala Ala Gln Lys Gly Ala Ser Leu Ile Ala Phe Pro Glu
            35              40              45

Val Phe Ile Pro Gly Tyr Pro Tyr Trp Ala Trp Leu Gly Asp Val Lys
    50              55              60

Tyr Ser Leu Ser Phe Thr Ser Arg Tyr His Glu Asn Ser Leu Glu Leu
65              70              75              80

Gly Asp Asp Arg Met Arg Arg Leu Gln Leu Ala Ala Arg Arg Asn Lys
                85              90              95

Ile Ala Leu Val Met Gly Tyr Ser Glu Arg Glu Ala Gly Ser Arg Tyr
            100             105             110

Leu Ser Gln Val Phe Ile Asp Glu Arg Gly Glu Ile Val Ala Asn Arg
    115             120             125

Arg Lys Leu Lys Pro Thr His Val Glu Arg Thr Ile Tyr Gly Glu Gly
130             135             140

Asn Gly Thr Asp Phe Leu Thr His Asp Phe Ala Phe Gly Arg Val Gly
145             150             155             160

Gly Leu Asn Cys Trp Glu His Val Gln Pro Leu Ser Lys Phe Met Met
                165             170             175

Tyr Ser Leu Gly Glu Gln Val His Val Ala Ser Trp Pro Ala Met Ser
            180             185             190

Pro Leu Gln Pro Asp Val Phe Gln Phe Ser Ile Glu Ala Asn Ala Thr
    195             200             205

Val Thr Arg Ser Tyr Ala Ile Glu Gly Gln Thr Phe Val Leu Cys Ser
210             215             220

Thr Gln Val Ile Gly Pro Ser Ala Ile Glu Thr Phe Cys Leu Asn Asp
225             230             235             240

Glu Gln Arg Ala Leu Leu Pro Gln Gly Gly Trp Ala Arg Ile Tyr
                245             250             255

Gly Pro Asp Gly Ser Glu Leu Ala Lys Pro Leu Ala Glu Asp Ala Glu
            260             265             270

Gly Ile Leu Tyr Ala Glu Ile Asp Leu Glu Gln Ile Leu Leu Ala Lys
    275             280             285

Ala Gly Ala Asp Pro Val Gly His Tyr Ser Arg Pro Asp Val Leu Ser
290             295             300

Val Gln Phe Asp Pro Arg Asn His Thr Pro Val His Arg Ile Gly Ile
305             310             315             320

Asp Gly Arg Leu Asp Val Asn Thr Arg Ser Arg Val Glu Asn Phe Arg
                325             330             335

Leu Arg Lys Ala Ala Glu Lys Glu Arg Gln Ala Ser Lys Arg Leu Gly
            340             345             350

Thr Lys Leu Phe Glu Gln Ser Leu Ala Glu Glu Pro Val Pro Ala
    355             360             365

Lys Leu Glu His His His His His
    370             375

<210> SEQ ID NO 9
<211> LENGTH: 1134
<212> TYPE: DNA
<213> ORGANISM: Acidovorax facilis

<400> SEQUENCE: 9

```
atggtatctt acaactccaa atttctggct gctaccgtac aggctgaacc ggtttggctg     60
gacgcggacg caactatcga taaatctatt ggtatcatcg aggaggcggc ccagaaaggt    120
gcgtctctga ttgccttccc ggaagttttc atccctggtt accgtattg ggcctggctg    180
ggtgacgtaa agtactccct gtccttcacc tcccgttacc acgaaaactc cctggaactg    240
ggtgacgacc gtatgcgccg tctgcaactg gctgcgcgtc gtaacaaaat cgcgctggtt    300
atgggttaca gcgagcgtga ggcaggcagc cgctacctgt cccaggtctt tatcgacgaa    360
cgtggtgaaa tcgttgctaa ccgtcgtaaa ctgaaaccaa ctcacgttga acgtacgatt    420
tatggtgaag caacggtac cgactttctg gtgcatgact cgcatttgg tcgtgttggt    480
ggtctgaact gctgggagca cgttcagccg ctgtccaaat tcatgatgta ctccctgggt    540
aacaggtac acgtcgcttc ttggccggct atgtccccgc tgcaaccgga cgtgtttcaa    600
ttttccatcg aggctaatgc gaccgtaacc cgctcctatg ctattgaagg ccaaaccttc    660
gttctggcgt ctacgcaggt tatcggtccg tctgcaattg aaaccttctg tctgaacgat    720
gagcaacgtg cactgctgcc gcagggtggc ggttgggcgc gtatctacgg cccggacggc    780
agcgaactgg ccaagccgct ggctgaagac gcagagggta ttctgtacgc agaaatcgat    840
ctggaacaga ttctgctggc caaggctggc gctgatccgg ttggtcacta cagccgccct    900
gatgtcctgt ccgtgcagtt cgacccgcgt aaccacaccc cggtacaccg cattggtatc    960
gatggccgtc tggatgttaa cacgcgttcc cgtgtagaaa actttcgcct gcgtaaagca   1020
gcagaaaaag aacgtcaggc cagcaaacgt ctgggcacga aactgtttga acagtctctg   1080
ctggcggagg agccggtacc agccaaactc gagcaccacc accaccacca ctga         1134
```

<210> SEQ ID NO 10
<211> LENGTH: 377
<212> TYPE: PRT
<213> ORGANISM: Acidovorax facilis

<400> SEQUENCE: 10

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Val His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Phe Ser Ile Glu Ala Asn Ala Thr
        195                 200                 205

Val Thr Arg Ser Tyr Ala Ile Glu Gly Gln Thr Phe Val Leu Ala Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
            325                 330                 335

Leu Arg Lys Ala Ala Glu Lys Glu Arg Gln Ala Ser Lys Arg Leu Gly
        340                 345                 350

Thr Lys Leu Phe Glu Gln Ser Leu Leu Ala Glu Glu Pro Val Pro Ala
    355                 360                 365

Lys Leu Glu His His His His His His
    370                 375

<210> SEQ ID NO 11
<211> LENGTH: 33
<212> TYPE: DNA
<213> ORGANISM: Artificial Sequence
<220> FEATURE:
<223> OTHER INFORMATION: synthesized

<400> SEQUENCE: 11
aggcagcctg tacctgtccc aggtctttat cga                                33

<210> SEQ ID NO 12
<211> LENGTH: 36
<212> TYPE: DNA
<213> ORGANISM: Artificial Sequence
<220> FEATURE:
<223> OTHER INFORMATION: synthesized

<400> SEQUENCE: 12
gacaggtaca ggctgcctgc ctcacgctcg ctgtaa                             36

<210> SEQ ID NO 13
<211> LENGTH: 35
<212> TYPE: DNA
<213> ORGANISM: Artificial Sequence
<220> FEATURE:
<223> OTHER INFORMATION: synthesized

<400> SEQUENCE: 13
cggtaccgac tttctggtgc atgacttcgc atttg                       35

<210> SEQ ID NO 14
<211> LENGTH: 35
<212> TYPE: DNA
<213> ORGANISM: Artificial Sequence
<220> FEATURE:
<223> OTHER INFORMATION: synthesized

<400> SEQUENCE: 14
caaatgcgaa gtcatgcacc agaaagtcgg taccg                       35

<210> SEQ ID NO 15
<211> LENGTH: 40
<212> TYPE: DNA
<213> ORGANISM: Artificial Sequence
<220> FEATURE:
<223> OTHER INFORMATION: synthesized

<400> SEQUENCE: 15
gaactgctgg gagcacgttc cgccgctgtc caaattcatg                  40

<210> SEQ ID NO 16
<211> LENGTH: 40
<212> TYPE: DNA
<213> ORGANISM: Artificial Sequence
<220> FEATURE:
<223> OTHER INFORMATION: synthesized

<400> SEQUENCE: 16
catgaatttg gacagcggcg gaacgtgctc ccagcagttc                  40

<210> SEQ ID NO 17
<211> LENGTH: 35
<212> TYPE: DNA
<213> ORGANISM: Artificial Sequence
<220> FEATURE:
<223> OTHER INFORMATION: synthesized

<400> SEQUENCE: 17
ccaaaccttc gttctggcgt ctacgcaggt tatcg                       35

<210> SEQ ID NO 18
<211> LENGTH: 35
<212> TYPE: DNA
<213> ORGANISM: Artificial Sequence
<220> FEATURE:
<223> OTHER INFORMATION: synthesized

<400> SEQUENCE: 18
cgataacctg cgtagacgcc agaacgaagg tttgg                       35

<210> SEQ ID NO 19
<211> LENGTH: 25
<212> TYPE: DNA
<213> ORGANISM: Artificial Sequence
<220> FEATURE:
<223> OTHER INFORMATION: synthesized

<400> SEQUENCE: 19
ctgccgcagg gtggcggttg ggcgc                                  25

<210> SEQ ID NO 20
<211> LENGTH: 25
<212> TYPE: DNA

```
<213> ORGANISM: Artificial Sequence
<220> FEATURE:
<223> OTHER INFORMATION: synthesized

<400> SEQUENCE: 20
gcgcccaacc gccaccctgc ggcag                                              25

<210> SEQ ID NO 21
<211> LENGTH: 42
<212> TYPE: DNA
<213> ORGANISM: Artificial Sequence
<220> FEATURE:
<223> OTHER INFORMATION: synthesized

<400> SEQUENCE: 21
gtattctgta cgcagaaatc ccgctggaac agattctgct gg                           42

<210> SEQ ID NO 22
<211> LENGTH: 42
<212> TYPE: DNA
<213> ORGANISM: Artificial Sequence
<220> FEATURE:
<223> OTHER INFORMATION: synthesized

<400> SEQUENCE: 22
ccagcagaat ctgttccagc gggatttctg cgtacagaat ac                           42

<210> SEQ ID NO 23
<211> LENGTH: 29
<212> TYPE: DNA
<213> ORGANISM: Artificial Sequence
<220> FEATURE:
<223> OTHER INFORMATION: synthesized

<400> SEQUENCE: 23
cgcagaaatc gatccggaac agattctgc                                          29

<210> SEQ ID NO 24
<211> LENGTH: 29
<212> TYPE: DNA
<213> ORGANISM: Artificial Sequence
<220> FEATURE:
<223> OTHER INFORMATION: synthesized

<400> SEQUENCE: 24
gcagaatctg ttccggatcg atttctgcg                                          29
```

US 11,987,826 B2

NITRILASE MUTANT AND APPLICATION THEREOF IN THE SYNTHESIS OF AN ANTI-EPILEPTIC DRUG INTERMEDIATE

The instant application contains a Sequence Listing which has been submitted electronically in the ASCII text file and is hereby incorporated by reference in its entirety. The ASCII text file is a sequence listing entitled "2023-07-26-Sequence_Lising" created on Jul. 26, 2023 and having a size of 26,736 bytes in compliance of 37 CFR 1.821.

TECHNICAL FIELD

The present invention relates to a nitrilase mutant derived from *Acidovorax facilis* CCTCC NO:M 209044 and its application in the synthesis of an anti-epileptic drug intermediate, 1-cyanocyclohexaneacetic acid.

BACKGROUND ART

Gabapentin was a novel antiepileptic drug developed by Warner-Lambert Company, USA. Compared with similar products on the market, it has fast oral absorption, less toxic and side effects, good therapeutic effect, and good tolerance. It does not bind to plasma proteins in vivo, does not induce liver enzymes, is not metabolized and so on. It can pass through the blood-brain barrier of human brains. It is very unlikely to interact with other anti-epileptic drugs, it is thus particularly effective as a superposition drug of intractable epilepsy.

1-Cyanocyclohexyl acetic acid is a key intermediate for synthesis of the anti-epileptic drug, gabapentin, the market prospect is very broad. At present, all the synthesis methods of gabapentin and its key intermediate 1-cyanocyclohexyl acetic acid adopt chemical synthesis technology, and there are problems of harsh reaction conditions, serious severe environmental pollution and high waste disposal costs, etc. in the production process.

Nitrilase (Nitrilase EC 3.5.5.1) is an enzyme that can directly hydrolyze nitriles (containing —CN) to the corresponding carboxylic acids. Reactions catalyzed by nitrilase has properties such as high stereoselectivity, high catalytic rate, mild reaction conditions and little environmental pollution, it is an environmentally friendly green synthesis method, and has important practical significance for energy conservation, emission reduction and building a harmonious society. At present, there are many examples of nitrilase in industrial applications, the product of BASF Company, Germany, (R)-mandelic acid, firstly, racemic mandelonitrile is formed by reaction of benzaldehyde and hydrocyanic acid, and then selecting an appropriate reaction condition, through nitrilase-catalyzed dynamic kinetic resolution, it quantitatively converts to (R)-mandelic acid. Methyleneglutaronitrile was first hydrolyzed to 4-cyanovaleric acid (4-CPA) ammonium salt by immobilized nitrilase-containing microbial cell catalyst (*Acidovorax facilis* 72W), the selectivity of the hydrolysis reaction was more than 98%, and its conversion rate was 100%, the reaction obtains one-half of ammonium cyanocarboxylate, and produces 1-2% of the only reaction by-product, 2-methylglutarate diammonium salt. Compared with traditional chemical methods, the chemical-enzymatic process has a higher yield, generates less waste, and has a higher stereoselectivity. In addition, many nitrilase enzymes have been developed and used in the synthesis of a variety of pharmaceutical intermediates and fine chemicals.

However, thermal stability of natural nitrilases is generally poor, which prevents its industrial application. The thermal stability of the enzyme can be improved by methods such as performing molecular modification or semi-rational design on the enzyme. Since crystal structure of the nitrilase has been reported little, modification on thermal stability of nitrilases has rarely been reported. Crum and Benedik et al. have studied thermal stability of Cyanidedihydratase (CynD$_{pum}$) derived from *Bacillus pumilus* for many years. The researchers firstly selected several forward mutating strains (K93R, D172N and E327K) by error-prone PCR, and subsequently fused the C-terminus of Cyanidedihydratase (CynD$_{stu}$) of *Pseudomonas stutzeri* and Cyanidedihydratase (CynD$_{pum}$), thereby improving its thermal stability (Frontiers in Microbiology 2016 Aug. 12; 7:1264.). Xu et al. carried out random mutation of AcN gene by error-prone PCR, thereby obtaining three mutants (AcN-T201L, AcN-Q339K, AcN-Q343K) with higher thermal stability. The pure enzyme was incubated at 45° C., sampled to measure the enzyme activity, and its half-life was calculated. It was found that the half-life of a multiple mutant AcN-T201F/Q339K/Q343K increased from 12.5 h to 180 h (Enzyme and Microbial Technology 113 (2018) 52-58). The nitrilase cloned from *Acidovorax facilis* CCTCC NO:M 029044 has been overexpressed in *Escherichia coli* BL21 (DE3), is capable of catalyzing 1-cyanocyclohexylacetonitrile to produce 1-cyanocyclohexyl acetic acid, and has pretty high catalytic activity on the substrate, 1-cyanocyclohexylacetonitrile through molecular modification (Catalysis Communications, 2015, 66, 121-125). 1-Cyanocyclohexylacetonitrile has a high solubility under high temperature conditions, which can promote the catalytic reaction, but the thermal stability of the catalytic enzyme is poor, and the catalytic activity is low under high temperature conditions, therefore, the existing nitrilase cannot meet the requirements, and it is necessary to improve the thermal stability of the nitrilase through molecular modification, thereby improving the catalytic efficiency and realizing industrial production.

SUMMARY OF THE INVENTION

The object of the present invention is to provide a nitrilase mutant protein with increased thermal stability and its application in the synthesis of 1-cyanocyclohexyl acetic acid, a recombinant vector containing the gene and a recombinant genetically engineering strain transformed by the recombinant vector, thereby solving the problem of poor thermal stability of nitrilase.

The present invention adopts the technical solution as follows:

The present invention provides a nitrilase mutant with increased thermal stability, wherein the mutant is obtained by mutating one or more of the amino acids at position 151, 223 and 205 of the amino acid sequence shown in SEQ ID No: 2.

Further, it is preferred that the mutant is obtained by: (1) mutating threonine at position 151 of the amino acid sequence shown in SEQ ID No: 2 into valine (T151V), and the amino acid sequence is shown in SEQ ID No: 4, and the nucleotide sequence of the encoding gene is shown in SEQ ID No: 3; (2) mutating cysteine at position 223 of the amino acid sequence shown in SEQ ID No: 2 into alanine (C223A), and the amino acid sequence is shown in SEQ ID No: 6, and the nucleotide sequence of the encoding gene is shown in SEQ ID No: 5; (3) mutating cysteine at position 250 of the amino acid sequence shown in SEQ ID No: 2 into glycine (C250G), and the amino acid sequence is shown in SEQ ID No: 8, and the nucleotide sequence of the encoding gene is shown in SEQ ID No: 7; or (4) mutating threonine at position 151, cysteine at position 223 and cysteine at position 250 of the amino acid sequence shown in SEQ ID No: 2 into valine, alanine and glycine, respectively, and the amino acid sequence is shown in SEQ ID No: 10, and the nucleotide sequence of the encoding gene is shown in SEQ ID No: 9.

The present invention also provides an engineered strain containing the encoding gene of the said nitrilase mutant.

In the preparation method of the nitrilase mutant of the present invention, any suitable vector can be used. For example, The suitable vector include but are not limited to prokaryotic expression vectors pET28, pET20, pGEX4T1, pTrC99A and pBV220, eukaryotic expression vectors pPIC9K, pPICZα, pYD1 and pYES2/GS, and clone vectors pUC18/19 and pBluscript-SK.

The present invention also provides an application of the nitrilase mutant in catalyzing an anti-epileptic drug intermediate, specifically the application of the nitrilase mutant in catalyzing 1-cyanocyclohexylacetonitrile to prepare 1-cyanocyclohexyl acetic acid, the application is carried out as follows: a reaction system is composed of a catalyst, a substrate and a reaction medium, wherein the catalyst is wet cells, wet cell-immobilized cells or a purified nitrilase, the wet wells are obtained by fermentation culture of a genetically engineered strain containing the nitrilase mutant, the purified nitrilase is obtained by subjecting the wet cells to ultrasonic breaking and then extraction, and the substrate is 1-cyanocyclohexylacetonitrile and the reaction medium is a pH=7.0, 200 mM disodium hydrogen phosphate-sodium dihydrogen phosphate buffer; the reaction is carried out in a constant temperature water bath at 25-50° C. (preferably 35° C.), after the reaction is completed, the reaction solution is subjected to separation and purification to obtain 1-cyanocyclohexyl acetic acid.

The final concentration of the substrate calculated by the amount of the substance per unit volume of the buffer is 100–1200 mM (preferably 1000-1200 mM), the amount of the catalyst calculated by the weight of the wet cells per unit volume of the buffer is 10-100 g/L, preferably 50 g/L.

Further, the wet cells are prepared according to the following method: the genetically engineered strain containing the encoding gene of the nitrilase mutant is inoculated into LB medium, cultured at 37° C. for 10-12 hours, the resulting inoculum is inoculated to LB medium containing kanamycin (with the final concentration of 50 mg/L) with 2% incubating volume and cultured at 37° C.; when OD600 of the culture medium reaches 0.6-0.8, isopropyl-β-D-thiogalactopyranoside is added with the final concentration of 0.1 mM, and the bacteria solution is subjected to induced expression at 28° C. for 10 hours; the cells are harvested by centrifugation and washed with normal saline twice, thereby obtaining the wet cells.

Further, the purified nitrilase is prepared according to the following method: (1) the wet cells are resuspended with a pH 8.0, 50 mM $NaH_2PO_4$ buffer containing NaCl with the final concentration of 300 mM and ultrasonic broken (400 W, 25 min, 1 s breaking, 1 s pause), the broken product is subjected to centrifugation (12000 rpm, 10 min), and the resulting supernatant is taken as a crude enzyme solution; (2) the crude enzyme solution is applied onto the Ni-NTA column at a flow rate of 1 mL/min which has been washed with an equilibrium buffer, an elution buffer is used at a flow rate of 2 mL/min to elute the weakly adsorbed protein impurities; then a protein elution buffer is used at a flow rate of 2 mL/min to elute and collect the target protein; (3) finally the obtained target protein is dialyzed with a 50 mM sodium dihydrogen phosphate-disodium hydrogen phosphate buffer as the dialysate, and the resulting retention is obtained which contains purified nitrilase; wherein the equilibrium buffer is a pH 8.0, 50 mM $NaH_2PO_4$ buffer containing NaCl with the final concentration of 300 mM, the elution buffer is a pH 8.0, 50 mM $NaH_2PO_4$ buffer containing NaCl and imidazole with the final concentrations of 300 mM and 50 mM, and the protein elution buffer is a pH 8.0, 50 mM $NaH_2PO_4$ buffer containing NaCl and imidazole with the final concentrations of 300 mM and 250 mM respectively.

Further, the wet cells are resuspended with a pH=7.0, 200 mM sodium dihydrogen phosphate-disodium hydrogen phosphate buffer, diatomite is added into the suspension with the final concentration of 6 mg/mL and stirred at room temperature for 1 h; subsequently, a polyethyleneimine aqueous solution with the mass concentration of 5% is added and stirred at room temperature for 1 hour; finally, a glutaraldehyde aqueous solution with the mass concentration of 25% is added and stirred for 0.5 hour, and the reaction solution is subjected to vacuum filtration, thereby obtaining the immobilized cells; wherein the volume of the polyethyleneimine aqueous solution is 3% of the volume of the buffer, the volume of the glutaraldehyde aqueous solution is 1% of the volume of the buffer.

In the present invention, the nitrilase mutant is used as a catalyst to catalyze the synthesis of 1-cyanocyclohexyl acetic acid, and Raney nickel is used to perform chemical catalytic hydrogenation of the 1-cyanocyclohexyl acetic acid to synthesize gabapentin-lactam, and then the gabapentin-lactam is hydrolyzed to produce gabapentin.

The specifically said nitrilase mutants of the present invention is obtained as follows: use semi-rational design, whole-plasmid PCR and molecular techniques to carry out site-directed mutation on a nitrilase-editing strain containing the encoding gene of the nitrilase shown in SEQ ID No: 1, E. coli BL21(DE3)/Pet28(+)-AcN-M derived from Acidovorax facilis) CCTCC NO: M 209044, subject the obtained strain to induced expression and screen out the positive mutants, thereby obtaining the mutants with increased thermal stability, which can catalyze regioselective hydrolysis of dinitrile to produce monocyanocarboxylic acid compound in a hotter environment.

The specifically said nitrilase mutants of the present invention as a catalyst may be the recombinant expression transformant (that is, wet cells, preferably E. coli BL21 (DE3)) containing the nitrilase mutant gene, the unpurified crude nitrilase, or the partially or completely purified nitrilase. If needed, it also can be immobilized enzyme or cells prepared from the nitrilase mutants of the present invention by immobilization techniques in the field.

In the present invention, the components of the LB liquid medium and the final concentrations thereof are as follows: 10 g/L tryptone, 5 g/L yeast extract, 10 g/L sodium chloride, water as solvent, natural pH. The components of LB solid medium and the final concentrations thereof are as follows: 10 g/L tryptone, 5 g/L yeast extract, 10 g/L sodium chloride, 20 g/L agar, water as solvent, natural pH.

Compared with the prior art, advantages of the present invention are mainly embodied in: in the present invention, by the semi-rational design and protein molecular modification, the thermal stability of the nitrilase mutant AcN-T151V/C223A/C250G was increased by up to 1.73 folds. The yield of the final product was up to 95% using the recombinant Escherichia coli containing the nitrilase mutant to hydrolyze 1M 1-cyanocyclohexylacetonitrile to produce 1-cyanocyclohexyl acetic acid at 35° C. And the yield of the final product was up to 97% when hydrolyzing 1.2M 1-cyanocyclohexylacetonitrile at 35° C. The final yield was up to 80% when using the nitrilase mutants obtained by the present invention to synthesize gabapentin. The mutants obtained by the present invention and its application laid the foundation for the highly efficient chemical enzymatic synthesis of gabapentin.

SPECIFIC EMBODIMENTS

Figure 1:
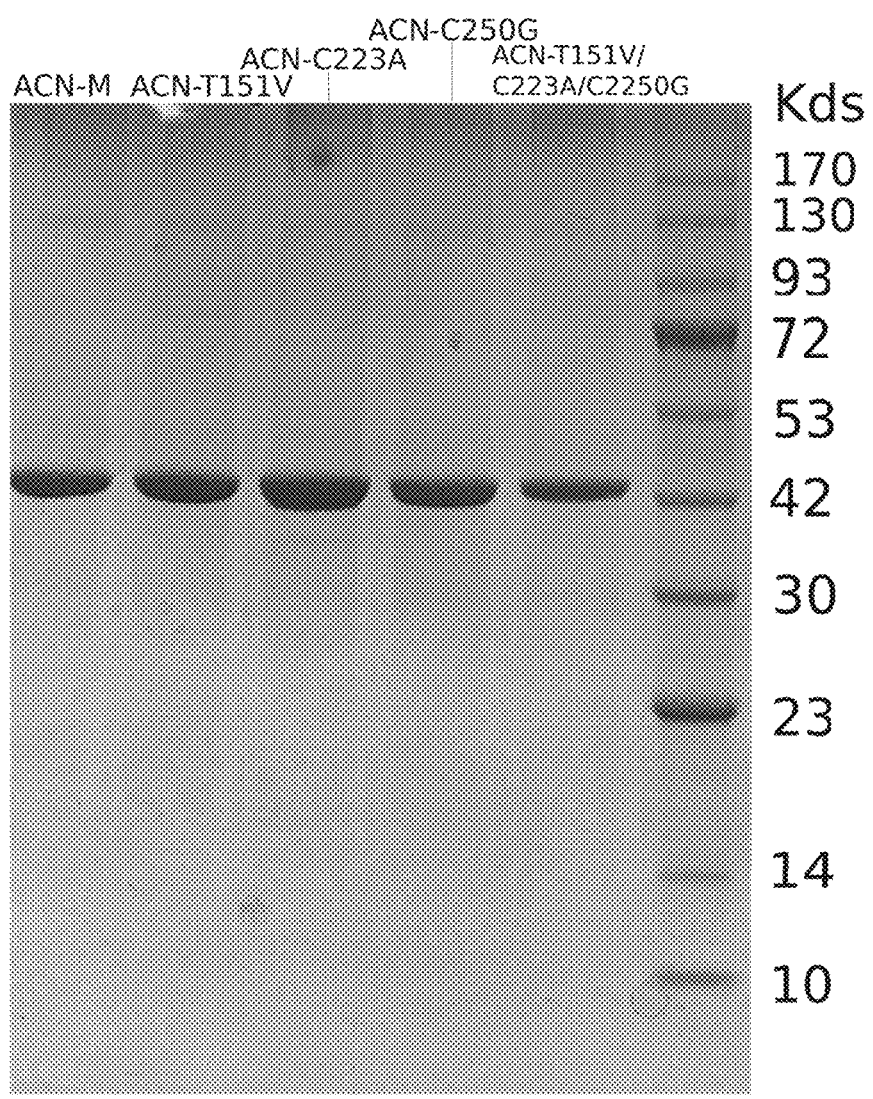
FIG. 1: an SDS-PAGE of the purified nitrilase proteins, wherein lane 1 is AcN-M, lane 2 is AcN-T151V, lane 3 is AcN-C223A, lane 4 is AcN-C250G, and lane 5 is AcN-T151V/C223A/C250G.

The present invention is further illustrated below with specific examples, but the scope of the present invention is not limited thereto:
The components of LB liquid medium and the final concentrations thereof are as follows: 10 g/L tryptone, 5 g/L yeast extract, 10 g/L sodium chloride, water as solvent, natural pH.
The components of LB solid medium and the final concentrations thereof are as follows: 10 g/L tryptone, 5 g/L yeast extract, 10 g/L sodium chloride, 15 g/L agar, water as solvent, natural pH.

Example 1: Semi-Rational Design and Site-Directed Mutation

The plasmid pET-28b(+)-AcN-M containing the nitrilase gene AcN-M (the nucleotide sequence is shown in SEQ ID No: 1, and the amino acid sequence is shown in SEQ ID No: 2) derived from *A. facilis* CCTCC NO:M 029044 was used as a template, the sites can improve the thermal stability, and site-directed mutation (table 1) was carried out by whole-plasmid PCR amplification. The PCR system (50 μL) was as follows: 0.5-20 ng of the template, 2×Phanta max Buffer 25 μL, 0.2 μM of each primer, Phanta Max Super-Fidelity DNA Polymerase 1 μL, water up to 50 μL. The PCR program was as follows: (1) pre-denaturation at 95° C. for 3 min; (2) denaturation at 95° C. for 15 s; (3) anneal at 60° C. for 15 s; (4) extension at 72° C. for 5.5 min, wherein steps (2)~(4) were cycled 30 times; and (5) finally, extension at 72° C. for 10 min, preservation at 16° C. The PCR product was identified by agarose gel electrophoresis, digested with DpnI, and then introduced into the host strain *E. coli* BL21 (DE3) which was then plated on a LB plate containing 50 ng/mL kanamycin to obtain monoclones. The monoclones were subjected to sequencing, and according to the results, a further verification was carried out by reaction.

TABLE 1 the design of the primers

| Name of the primers | sequences of the primers (5' to 3') |
|---|---|
| R111L-F | AGGCAGCCTGTACCTGTCCCAGGTCTTTATCGA |
| R111L-R | GACAGGTACAGGCTGCCTGCCTCACGCTCGCTGTAA |
| T151V-F | CGGTACCGACTTTCTGGTGCATGACTTCGCATTTG |
| T151V-R | CAAATGCGAAGTCATGCACCAGAAAGTCGGTACCG |
| Q169P-F | GAACTGCTGGGAGCACGTTCCGCCGCTGTCCAAATTCATG |
| Q169P-R | CATGAATTTGGACAGCGGCGGAACGTGCTCCCAGCAGTTC |
| C223A-F | CCAAACCTTCGTTCTGGCGTCTACGCAGGTTATCG |
| C223V-R | CGATAACCTGCGTAGACGCCAGAACGAAGGTTTGG |
| C250G-F | CTGCCGCAGGGTGGCGGTTGGGCGC |
| C250G-R | GCGCCCAACCGCCACCCTGCGGCAG |
| D280P-F | GTATTCTGTACGCAGAAATCCCGCTGGAACAGATTCTGCTGG |
| D280P-R | CCAGCAGAATCTGTTCCAGCGGGATTTCTGCGTACAGAATAC |
| L281P-F | CGCAGAAATCGATCCGGAACAGATTCTGC |
| L281P-R | GCAGAATCTGTTCCGGATCGATTTCTGCG |

T151V, C223A and C250G, the mutants with increased thermal stability were screened out with liquid chromatography whose nucleotide sequences are shown in SEQ ID No: 3, SEQ ID No: 5 and SEQ ID No: 7, respectively. And with the same method, the combinatorial mutant T151V/C223A/C250G was constructed, and the nucleotide sequence is shown in SEQ ID No: 9.

The above mutants and the original vector were respectively transformed into *E. coli* BL21(DE3) to construct the single mutants *E. coli* BL21(DE3)/pET28b(+)-AcN-T151V, *E. coli* BL21(DE3)/pET28b(+)-AcN-C223A and *E. coli* BL21(DE3)/pET28b(+)-AcN-C250G, the combinatorial mutant *E. coli* BL21(DE3)/pET28b(+)-AcN-T151V/C223A/C250G and the original strain *E. coli* BL21(DE3)/pET28b(+)-AcN-M.

Example 2: Expression of the Nitrilase Mutant

The single mutants *E. coli* BL21(DE3)/pET28b(+)-AcN-T151V, *E. coli* BL21(DE3)/pET28b(+)-AcN-C223A and *E. coli* BL21(DE3)/pET28b(+)-AcN-C250G, the combinatorial mutant *E. coli* BL21(DE3)/pET28b(+)-AcN-T151V/C223A/C250G and the original strain *E. coli* BL21(DE3)/pET28b(+)-AcN-M obtained in Example 1 were respectively inoculated to LB medium and cultured at 37° C. for 10-12h, the resulting inocula were respectively inoculated to LB medium containing kanamycin (with the final concentration of 50 mg/L) with 2% incubating volume, amplified and cultured at 37° C. When OD600 of the culture medium reached 0.6-0.8, isopropyl-β-D-thiogalactopyranoside (IPTG) was added with the final concentration of 0.1 mM to carry out induced expression at 28° C. for 10 hours. The wet cells were harvested by centrifugation and washed with normal saline twice.

Example 3: Purification of the Nitrilase Mutants (1) Binding buffer (50 mM NaH$_2$PO$_4$, 300 mM NaCl, pH 8.0) was added to the wet cells obtained in example 2, the cells were resuspended, ultrasonic broken (400 W, 25 min, 1 s breaking, 1 s pause) and centrifuged (12000×g, 10 min). The supernatant was a crude enzyme solution for separation and purification.
(2) After pre-filling a 20 mL Ni-NTA affinity column, an equilibrium buffer (50 mM NaH$_2$PO$_4$, 300 mM NaCl, pH 8.0) was used to equilibrate the column at a flow rate of 2 mL/min.
(3) After the Ni-NTA column was washed with 8-10 column volume, the obtained crude enzyme solution was applied onto the Ni-NTA column at a flow rate of 1 mL/min, and the target protein bound to the column. After loading, a large amount of unbound protein impurities which did not bind to the resin would be directly removed.
(4) An equilibrium buffer (50 mM NaH$_2$PO$_4$, 300 mM NaCl, 50 mM imidazole, pH 8.0) was used to elute the weakly adsorbed protein impurities at a flow rate of 2 mL/min.
(5) A protein elution buffer (50 mM NaH$_2$PO$_4$, 300 mM NaCl, 250 mM imidazole, pH 8.0) was used to elute and collect the target protein at a flow rate of 2 mL/min.
(6) The collected enzyme solution was dialyzed with a dialysis bag (Economical Biotech Membrane, 14KD, purchased from Sangon Biotech (Shanghai) Co., Ltd.) with a sodium dihydrogen phosphate-disodium hydrogen phosphate buffer (50 mM, pH 7.0) as the dialysate, and the resulting retention was obtained which contained the purified nitrilase solution.
(7) The purified proteins were analyzed by SDS-PAGE, and the results of protein electrophoresis are shown in FIG. 1.

Example 4 Activity Determination of the Nitrilases

Figure 8:
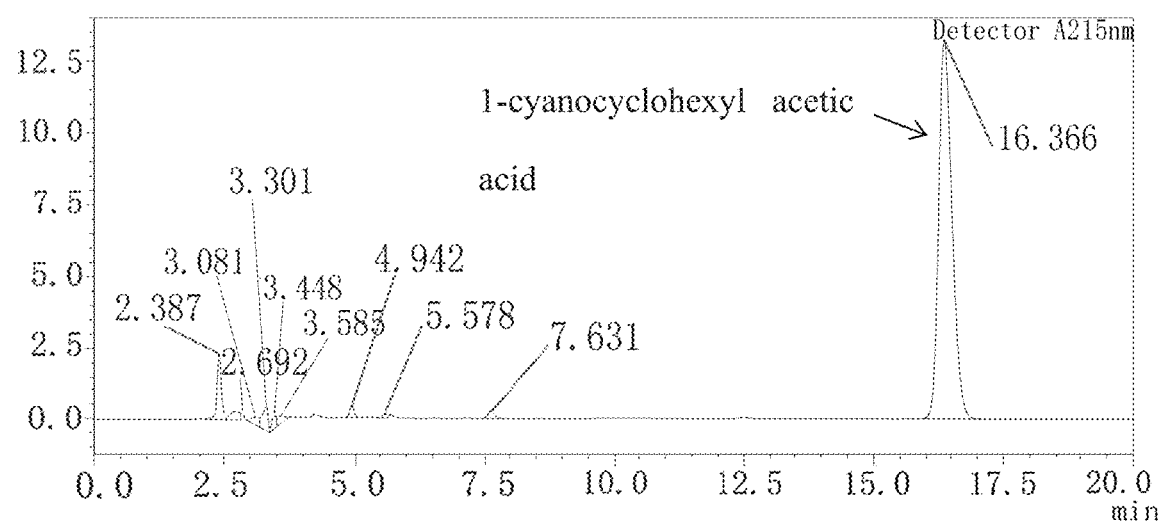
FIG. 8: high performance liquid chromatogram of 1-cyanocyclohexyl acetic acid

The activity of the purified nitrilases from example 3 was determined. A reaction system (10 mL) for nitrilase activity assay was as follows: a sodium dihydrogen phosphate-disodium hydrogen phosphate buffer (200 mM, pH 7.0), 200 mM 1-cyanocyclohexylacetonitrile, and 0.4 mg of the purified nitrilase solution. The reaction solution was preheated at 35° C. for 10 min and then reacted at 180 rpm for 10 min. 200 μL of the supernatant was sampled, and 4 μL of 6M HCl was added to terminate the reaction, the conversion rate of 1-cyanocyclohexyl acetic acid was determined by liquid chromatography (Shimadzu LC-16) external standard method, and the high performance liquid chromatogram of the 1-cyanocyclohexyl acetic acid is shown in FIG. 8.

The column was J&KCHEMICA®C-18 column (250 mm×4.6 mm, 5 μm), and the mobile phase was a buffer (0.58 g/L diammonium phosphate, 1.83 g/L sodium perchlorate, pH was adjusted to 1.8 by perchloric acid, the solvent was deionized water and acetonitrile in a ratio of 76:24 (v/v), the flow rate was 1 mL/min, the ultraviolet detection wavelength was 215 nm, and the column temperature was 40° C.

Figure 2:
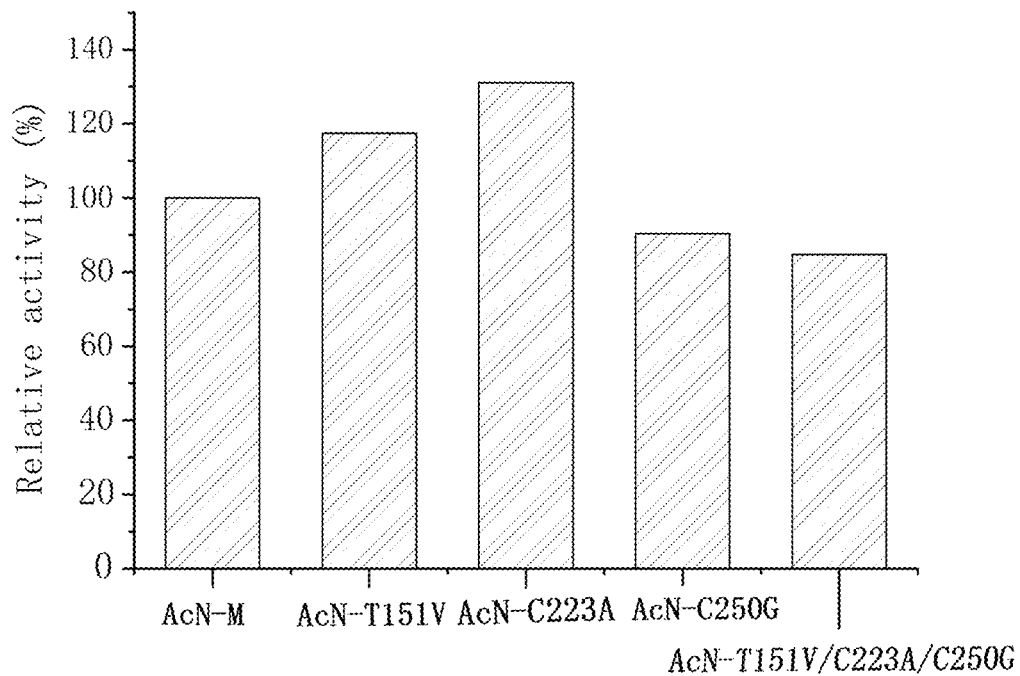
FIG. 2: activity comparison of the nitrilase mutants.

Enzyme activity definition (U): the amount of enzyme required to catalyze the formation of 1 μmol of 1-cyanocyclohexyl acetic acid per minute at 35° C., in a pH 7.0, 100 mM sodium dihydrogen phosphate-disodium hydrogen phosphate buffer was defined as 1 U. The relative activity of the mutants, AcN-T151V and AcN-C223A was 1.17 and 1.31 times that of the original nitrilase AcN-M, and the initial activity of the mutant AcN-C250G and the combinatorial mutant AcN-T151V/C223A/C250G was only 90.38% and 84.71% that of the original nitrilase AcN-M, the results are shown in FIG. 2.

Example 5: Determination of Thermal Stability of the Nitrilase Mutant at 50° C.

Figure 3:
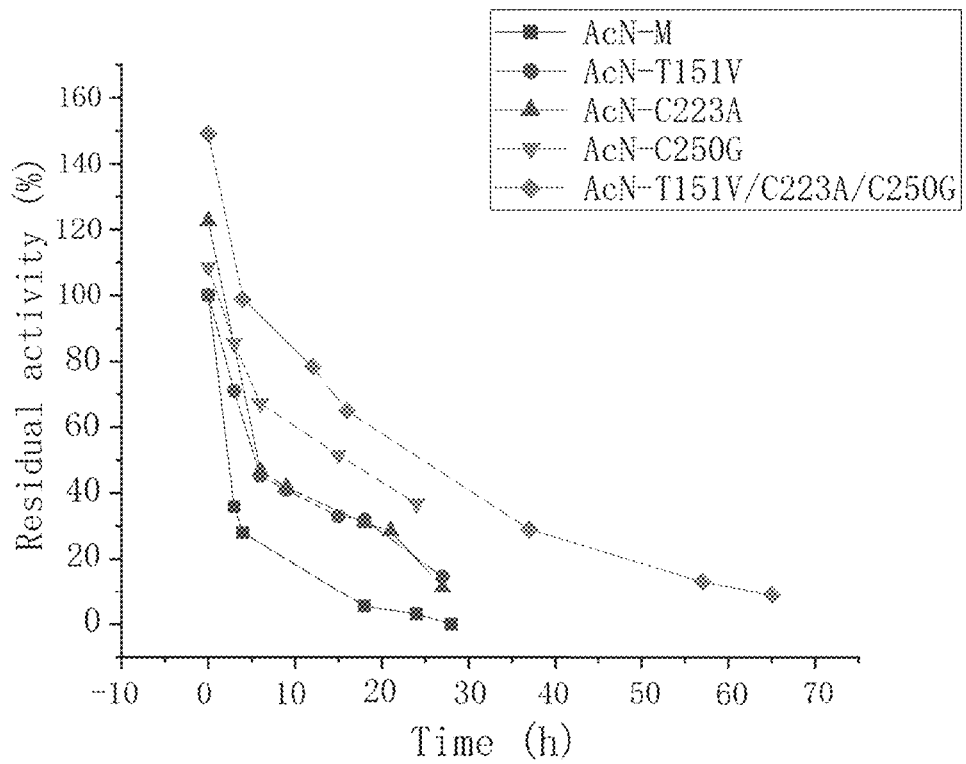
FIG. 3: thermal stability of the nitrilase mutants at 50° C.

The thermal stability of the purified nitrilases from example 3 was measured. A certain amount of the purified nitrilases was taken into a 50 mL sterile polypropylene centrifuge tube and stored in a constant temperature water bath at 50° C. The proteins were sampled for measurement of activity of the protein at different time intervals according to the method as described in example 4. With the activity of the protein before the storing as a control, residual activities (referred to as RA) of the proteins at every time interval were calculated. With time (h) as the abscissa and the natural logarithm of the relative residual activity (Ln (RA)) as the ordinate, linear fitting was performed (the results are shown in FIG. 3), and the slope k was obtained. According to the formula of one-step inactivation model $$t_{\frac{1}{2}} = \frac{Ln2}{k},$$

the half-life of the enzyme protein $$t_{\frac{1}{2}}$$

can be obtained.

The half-life of the original nitrilase AcN-M was determined to be 13.6 h, the half-life of the mutant AcN-T151V was 14 h, the half-life of the mutant AcN-C223A was 14.2 h, the half-life of the mutant AcN-C250G was 19.9 h, the half-life of the combinatorial mutant T151V/C223A/C250G was 23.6 h, and the results are shown in FIG. 2.

TABLE 2 the half-life of the nitrilase mutants at 50° C.

| nitrilase | thermal stability at 50° C. (h) |
| --- | --- |
| AcN-M | 13.6 ± 1.5 |
| AcN-T151V | 14 ± 2 |
| AcN-C223A | 14.2 ± 2 |
| AcN-C250G | 19.9 ± 2 |
| AcN-T151V/C223A/C250G | 23.6 ± 2 |

Figure 4:
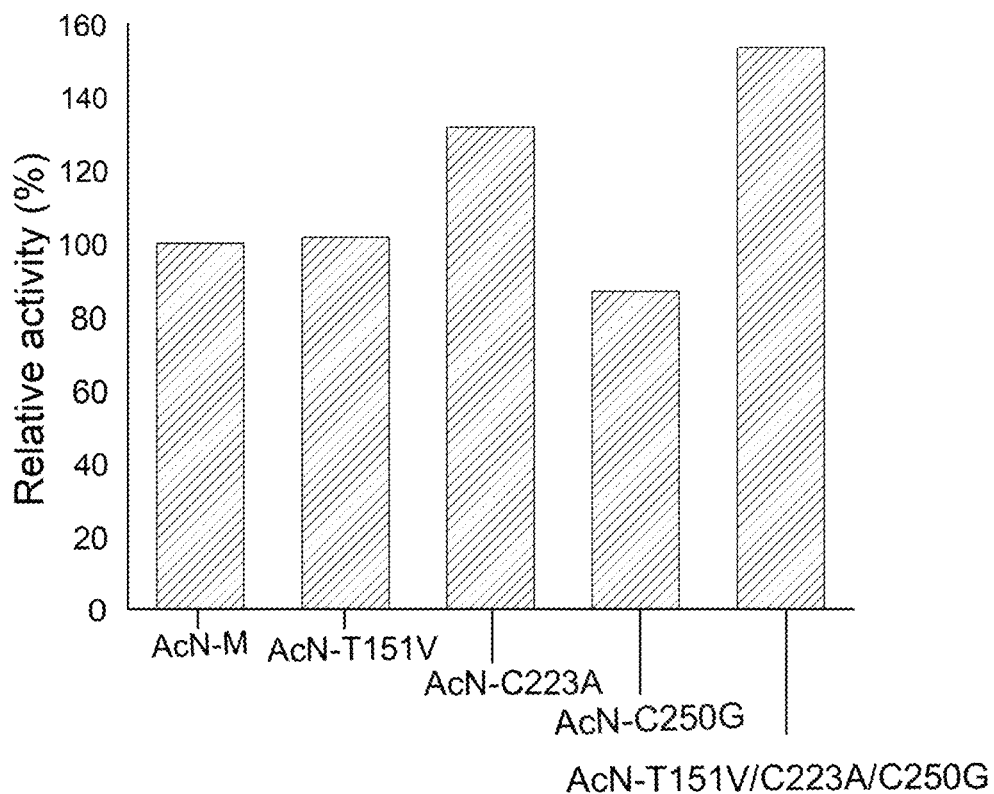
FIG. 4: activity comparison of recombinant *E. coli* resting cells containing the nitrilase mutants.

Example 6: Activity Determination of the Recombinant *E. coli* Containing the Nitrilase The recombinant *E. coli* BL21(DE3)/pET28b(+)-AcN-T151V, *E. coli* BL21(DE3)/pET28b(+)-AcN-C223A and *E. coli* BL21(DE3)/pET28b(+)-AcN-C250G, the combinatorial mutant *E. coli* BL21(DE3)/pET28b(+)-AcN-T151V/C223A/C250G and the original strain *E. coli* BL21(DE3)/pET28b(+)-AcN-M obtained by cultivation in example 2 were subjected to activity determination. A reaction system (10 mL) for nitrilase activity assay was as follows: a sodium dihydrogen phosphate-disodium hydrogen phosphate buffer (200 mM, pH 7.0), 200 mM 1-cyanocyclohexylacetonitrile, and 10 g/L the wet cells of the recombinant *E. coli*. The reaction solution was preheated at 35° C. for 10 min and then reacted at 180 rpm for 10 min. 200 μL of the supernatant was sampled, the conversion rate of 1-cyanocyclohexyl acetic acid was determined by liquid chromatography (Shimadzu LC-16) external standard method under the same conditions in example 4. The relative activity of *E. coli* BL21(DE3)/pET28b(+)-AcN-T151V. *E. coli* BL21(DE3)/pET28b(+)-AcN-C223A and *E. coli* BL21(DE3)/pET28b(+)-AcN-T151V/C223A/C250G, the recombinant *E. coli* strains containing the corresponding nitrilase mutant, was 1.02, 1.32 and 1.54 times that of the original strain *E. coli* BL21(DE3)/pET28b(+)-AcN-M, however, the initial activity of *E. coli* BL21(DE3)/pET28b(+)-AcN-C250G was only 86.9% that of the original strain *E. coli* BL21(DE3)/pET28b(+)-AcN-M, the results are shown in FIG. 4.

Example 7: Determination of Thermal Stability of the Recombinant *E. coli* Containing the Nitrilase Mutants at 50° C.

Figure 5:
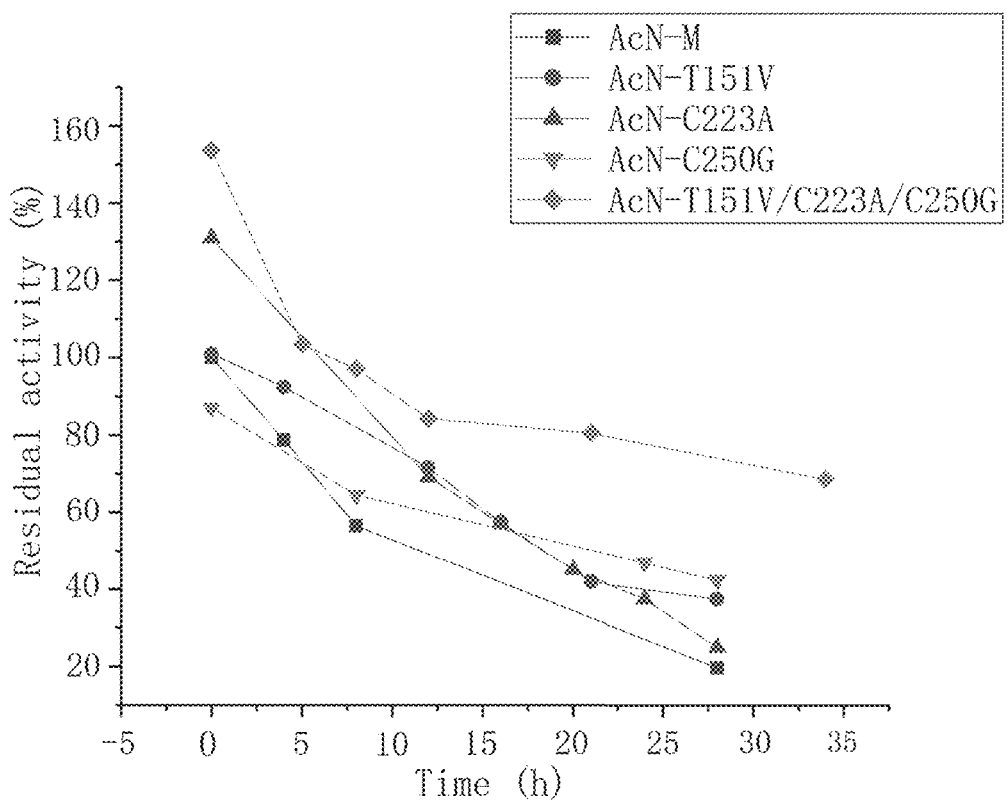
FIG. 5: thermal stability of recombinant *E. coli* resting cells containing the nitrilase mutants at 50° C.

The resting cells of the recombinant *E. coli* containing the nitrilase mutants, *E. coli* BL2 (DE3)/pET28b(+)-AcN-T151V, *E. coli* BL21(DE3)/pET28b(+)-AcN-C223A and *E. coli* BL21(DE3)/pET28b(+)-AcN-C250G, the combinatorial mutant *E. coli* BL21(DE3)/pET28b(+)-AcN-T151V/C223A/C250G and the original strain *E. coli* BL21(DE3)/pET28b(+)-AcN-M, obtained in example 2, were respectively suspended in sodium dihydrogen phosphate-disodium hydrogen phosphate buffer (200 mM, pH 7.0) to obtain a 100 g/L bacterial suspension, and stored in a constant temperature water bath at 50° C. The bacterial suspension was sampled for measurement of activity of the resting cells at different time intervals according to the method as described in example 6. With the activity of the resting cells before stored in a constant temperature water bath at 50° C. as a control, residual activities of the resting cells at each time interval were calculated, and the results were shown in FIG. 5.

Example 9: Hydrolysis of 1M 1-cyanocycloalkaneacetonitrile by the Recombinant *E. coli* Containing the Nitrilase Mutant 0.5 g of wet cells of *E. coli* the combinatorial mutant *E. coli* BL21(DE3)/pET28b(+)-AcN-T151V/C223A/C250G and the original strain *E. coli* BL21(DE3)/pET28b(+)-AcN-M, obtained by the method as described in example 2, were suspended in 10 mL of sodium dihydrogen phosphate-disodium hydrogen phosphate buffer (200 mM, pH 7.0) respectively, 1.48 g of 1-cyanocyclohexylacetonitrile was added with the final concentration of 1M, and the reaction was carried out in a constant temperature water bath at 35° C. The reaction solution was sampled at different time intervals, centrifuged at 12000 rpm, and the precipitates were discarded. The supernatant was analyzed for the concentration of the product by high performance liquid chromatography. The HPLC conditions were as described in example 4.

Figure 6:
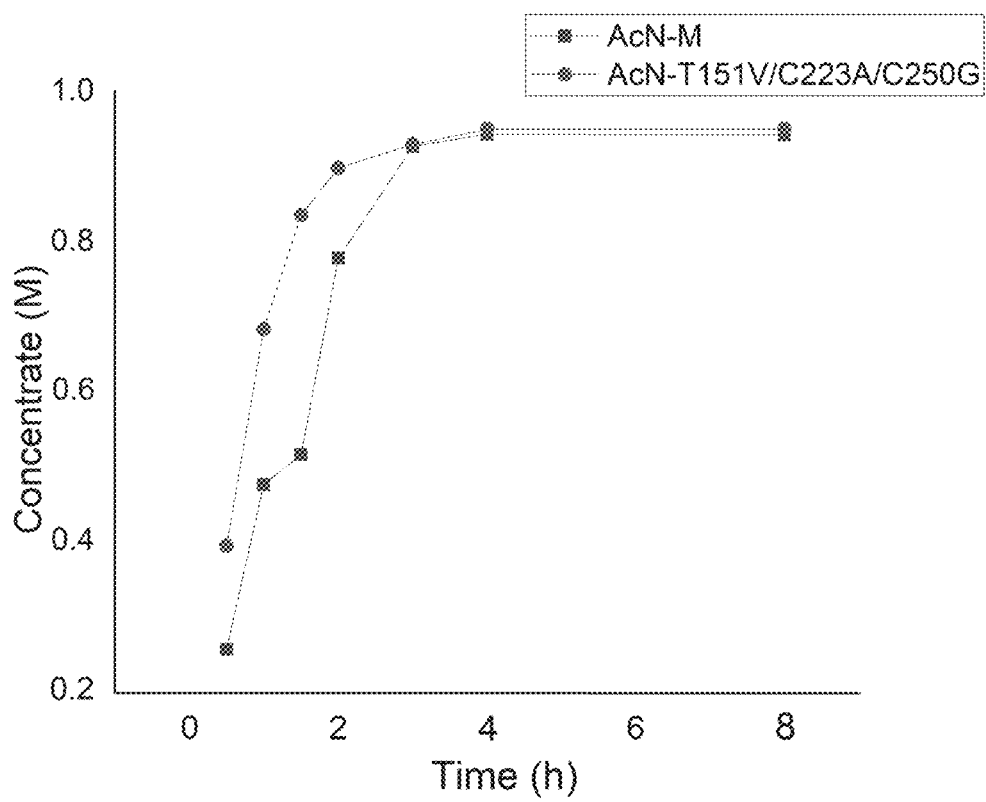
FIG. 6: comparison of hydrolysis of 1M 1-cyanocycloalkaneacetonitrile by recombinant *E. coli* resting cells containing the nitrilase mutants.

As shown in FIG. 6, the mutant, *E. coli* BL21(DE3)/pET28b(+)-AcN-AcN-T151V/C223A/C250G could completely hydrolyze the substrate within 2 h, which was much faster than *E. coli* BL21(DE3)/pET28b(+)-AcN-M.

Example 10: Hydrolysis of 1.2 M 1-cyanocycloalkaneacetonitrile by the Recombinant *E. coli* Containing the Nitrilase Mutant 0.5 g of wet cells of the combinatorial mutant *E. coli* BL21(DE3)/pET28b(+)-AcN-T151V/C223A/C250G and the original strain *E. coli* BL21(DE3)/pET28b(+)-AcN-M, obtained by the method as described in example 2, were suspended in 10 mL of sodium dihydrogen phosphate-disodium hydrogen phosphate buffer (200 mM, pH 7.0) respectively, 1.78 of 1-cyanocyclohexylacetonitrile was added with the final concentration of 1.2M, and the reaction was carried out in a constant temperature water bath at 35° C. The reaction solution was sampled at different time intervals, centrifuged at 12000 rpm, and the precipitates were discarded. The supernatant was analyzed for the concentration of the product by high performance liquid chromatography. The HPLC conditions were as described in example 4.

Figure 7:
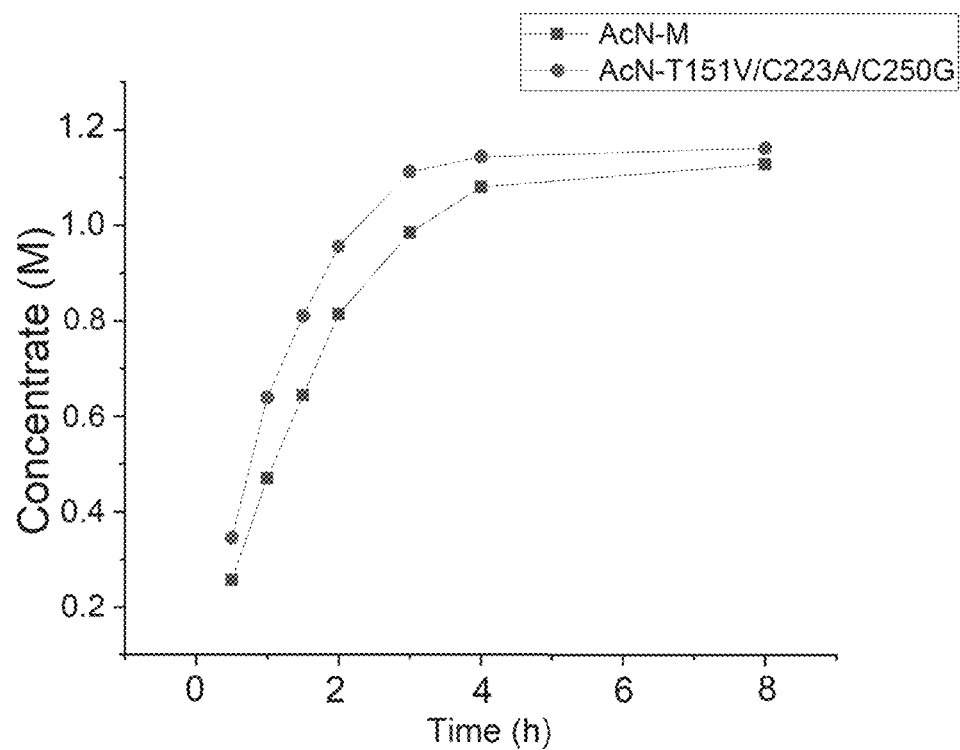
FIG. 7: comparison of hydrolysis of 1.2 M 1-cyanocycloalkaneacetonitrile by recombinant *E. coli* resting cells containing the nitrilase mutants.

As shown in Table 3, the mutant, *E. coli* BL21(DE3)/pET28b(+)-AcN-AcN-T151V/C223A/C250G could completely hydrolyze the substrate within 4 h, which was much faster than *E. coli* BL21(DE3)/pET28b(+)-AcN-M. The results are shown in FIG. 7.

TABLE 3 hydrolysis of 1.2 M 1-cyanocycloalkaneacetonitrile by the recombinant *E. coli* containing the nitrilase mutant

| strains | reaction temperature (° C.) | reaction time (h) | yield (%) |
| --- | --- | --- | --- |
| *E. coli* BL21(DE3)/pET28b(+)-AcN-M | 35 | 4 | 95 |
| *E. coli* BL21(DE3)/pET28b(+)-AcN-T151V/C223A/C250G | 35 | 4 | 99 |

Example 11: Hydrolysis of 1 M 1-cyanocycloalkaneacetonitrile by the Immobilized Cells 2 g of the wet cells of the combinatorial mutant *E. coli* BL21(DE3)/pET28b(+)-AcN-T151V/C223A/C250G and the original strain *E. coli* BL21(DE3)/pET28b(+)-AcN-M, obtained by the method as described in example 2, were suspended in 20 mL of sodium dihydrogen phosphate-disodium hydrogen phosphate buffer (200 mM, pH 7.0), diatomite was added into the suspension with the final concentration of 0.006 g/mL, and the mixture was stirred at room temperature for 1 h. Subsequently, a 5% (w/w) polyethyleneimine aqueous solution was added into the mixture, and stirred at room temperature for 1 hour. Finally, a 25% (w/w) glutaraldehyde aqueous solution was added and the mixture was stirred for 0.5 hour, and the immobilized cells were obtained by vacuum filtration. Wherein, the volume of the polyethyleneimine aqueous solution was 3% of the volume of the buffer, and the volume of the glutaraldehyde aqueous solution was 1% of the volume of the buffer.

Immobilized cells prepared from 0.5 g of the wet cells were suspended in 10 mL of sodium dihydrogen phosphate-disodium hydrogen phosphate buffer (200 mM, pH 7.0), 1.48 g of 1-cyanocyclohexylacetonitrile was added (with the final concentration of 1 M) and the reaction was carried out in a constant temperature water bath at 25° C. Wherein, the immobilized cells prepared from the original strain *E. coli* BL21(DE3)/pET28b(+)-AcN-M was subjected to the reaction for 7-8 hours per batch, the immobilized cells prepared from E. coli BL21(DE3)/pET28b(+)-AcN-T151V/C223A/C250G was subjected to the reaction for 4-6 hours per batch. After the completion of each batch of the reaction, vacuum filtration was carried out for the solid-liquid separation, and the resulting reaction solution was analyzed by high performance liquid chromatography for profiling the concentration of the product according to the method described in example 4, and the immobilized cells were taken out and applied into the next batch of reaction. The results were shown in Table 4.

TABLE 4 hydrolysis of 1 M 1-cyanocycloalkaneacetonitrile by the immobilized cells

| Strains | reaction time per batch (h) | conversion rate (%) | number of batches |
|---|---|---|---|
| E. coli BL21(DE3)/pET28b(+)-AcN-M | 7-8 | >99 | 5 |
| E. coli BL21(DE3)/pET28b(+)-AcN-T151V/C223A/C250G | 4-6 | >99 | 7 |

Example 12: Treatment of 1-Cyanocyclohexyl Acetic Acid by Flocculence Method 1.245 kg of the reaction solution from example 11 was added with 1% polyaluminum chloride to flocculate for 4 h and 1% diatomite to adsorb for 2 h, the mixture was filtrated with Buchner funnel to obtain the filtrate, the filtrate was added with a certain amount of hydrochloric acid to adjust the pH to about 2.0 and an equal volume of dichloromethane, and stirred in a three-necked flask for 20 minutes, then the reaction solution was transferred to a separatory funnel, and allowed to stand for about 10 minutes for separation, the lower layer was taken out, spin steamed and dried in an oven, thereby obtaining 158 g of solid 1-cyanocyclohexyl acetic acid.

Example 13: Synthesis of Gabapentin from 1-Cyanocyclohexyl Acetic Acid by Chemical Method 78.3 g of the 1-cyanocyclohexyl acetic acid from example 12 was dissolved in water and added with sodium hydroxide solution to adjust the pH to about 10, the concentration to 1M and the volume to 470 mL. The resulting solution was added with 20% Raney nickel catalyst, reacted under the conditions of 110° C., 2.0 MPa, 450 rpm and hydrogenation for about 4-5 h, and filtered while hot to obtain 582.5 g of hydrogenation conversion liquid. The hydrogenation conversion liquid was put in a three-necked flask, added with hydrochloric acid to adjust the pH to about neutral, and heat reflux reacted at 100° C. for about 4 h. The resulting solution was extracted with dichloromethane, rotary steamed and dried, thereby obtaining 56.3 g of solid gabapentin-lactam. The yield of this step was about 81%.

15.3 g g of the gabapentin-lactam was dissolved in 50 ml of HCl solution, heat reflux reacted at 150 rpm for about 4 h, and naturally cooled to room temperature. The unreacted gabapentin-lactam was extracted with dichloromethane, the water phase was cooled at 0-4° C. for 1 hour, then filtered to obtain white crystals, and dried at 40° C. to obtain gabapentin hydrochloride. The mother liquor was recycled and reused. 36.4 g of the gabapentin was dissolved in 50 ml water at 40° C., then 12.5 ml toluene was added, and the pH was adjusted to 7.0-7.5 with 200 g/L sodium carbonate, stirred for 30 min, then recrystallized with methanol or isopropanol to obtain pure gabapentin. The mother liquor was recycled again for the next crystallization and purification, and the final yield of gabapentin reached 80%.

The invention claimed is:

1. A nitrilase mutant, wherein the nitrilase mutant has nitrilase activity and comprises the amino acid sequence of SEQ ID NO: 2, except for the substitution T151V, the substitution C223A, or the substitutions T151V, C223A, and C250G.

2. A polynucleotide comprising a nucleotide sequence encoding the nitrilase mutant of claim 1.

3. A method for producing 1-cyanocyclohexyl acetic acid, the method comprising:
reacting a catalyst and a substrate in a reaction medium to produce a reaction solution comprising 1-cyanocyclohexyl acetic acid,
wherein the catalyst is
wet cells comprising the nitrilase mutant of claim 1, wherein the wet wells are obtained by fermentation culture of a genetically engineered strain expressing the nitrilase mutant,
immobilized cells comprising the nitrilase mutant, or
the nitrilase mutant, wherein the nitrilase mutant is purified, wherein the purified nitrilase mutant is obtained by subjecting the wet cells to ultrasonic breaking and centrifugation,
wherein the substrate is 1-cyanocyclohexylacetonitrile,
wherein the reaction medium is a pH 7.0, 200 mM disodium hydrogen phosphate-sodium dihydrogen phosphate buffer,
wherein the reaction is carried out in a constant temperature water bath at 25-50° C., and
wherein after the reaction is completed, the reaction solution is subjected to separation and purification to obtain 1-cyanocyclohexyl acetic acid.

4. The method of claim 3, wherein the final concentration of the substrate in the reaction medium is 100-1200 mM, wherein the catalyst is wet cells and the concentration of wet cells in the reaction medium is 10-100 g/L.

5. The method of claim 3, wherein the reaction temperature is 35° C.

6. The method of claim 3, wherein the wet cells are prepared according to the following method:
   culturing LB medium with the genetically engineered strain expressing the nitrilase mutant at 37° C. for 10-12 hours to produce an inoculum,
   inoculating LB medium with the inoculum with a 2% incubating volume, wherein the LB medium contains 50 mg/L kanamycin, and culturing at 37° C.,
   inducing expression of the nitrilase mutant by adding isopropyl-p-D-thiogalactopyranoside to a final concentration of 0.1 mM when the $OD_{600}$ of the culture medium reaches 0.6-0.8 and culturing at 28° C. for 10 hours,
   harvesting cells by centrifugation, and
   washing the cells with normal saline twice thereby obtaining the wet cells.

7. The method of claim 6, wherein the purified nitrilase is prepared according to the following method:
   resuspending the wet cells with a pH 8.0, 50 mM $NaH_2PO_4$ buffer containing 300 mM NaCl,
   ultrasonically breaking the resuspended wet cells under the conditions of 400 W, 25 min, 1 s breaking and 1 s pause,
   centrifuging the broken cells at 12000 rpm for 10 min to obtain a supernatant, wherein the supernatant is a crude enzyme solution,
   applying the crude enzyme solution to a Ni-NTA column that has been washed with an equilibrium buffer, wherein the crude enzyme solution is applied to the Ni-NTA column at a flow rate of 1 mL/min, and wherein the equilibrium buffer is a pH 8.0, 50 mM $NaH_2PO_4$ buffer containing 300 mM NaCl,
   applying a first elution buffer to the Ni-NTA column with the applied crude enzyme solution at a flow rate of 2 mL/min to elute weakly adsorbed protein impurities, wherein the first elution buffer is a pH 8.0, 50 mM $NaH_2PO_4$ buffer containing 300 mM NaCl and 50 mM imidazole,
   applying a second elution buffer to the Ni-NTA column with the applied first elution buffer at a flow rate of 2 mL/min to elute and collect the nitrilase mutant, wherein the second elution buffer is a pH 8.0, 50 mM $NaH_2PO_4$ buffer containing 300 mM NaCl and 250 mM imidazole, and
   dialyzing the collected nitrilase mutant with a 50 mM sodium dihydrogen phosphate-disodium hydrogen phosphate buffer.

8. The method of claim 6, wherein the immobilized cells are prepared according to the following method:
   resuspending the wet cells with a pH 7.0, 200 mM sodium dihydrogen phosphate-disodium hydrogen phosphate buffer to form a cell suspension,
   adding diatomite into the cell suspension to a final concentration of 6 mg/mL and stirring at room temperature for 1 hour to form a cell suspension comprising diatomite,
   adding a 5% polyethyleneimine aqueous solution with a mass concentration of 5% to the cell suspension comprising diatomite and stirring at room temperature for 1 hour to form a cell suspension comprising diatomite and polyethyleneimine, wherein the volume of the polyethyleneimine aqueous solution is 3% of the volume of the cell suspension comprising diatomite and polyethyleneimine,
   adding a glutaraldehyde aqueous solution with a mass concentration of 25% to the cell suspension comprising diatomite and polyethyleneimine and stirring for 0.5 hour to form an immobilization reaction solution, wherein the volume of the glutaraldehyde aqueous solution is 1% of the volume of the immobilization reaction solution, and
   subjecting the immobilization reaction solution to vacuum filtration to thereby obtain the immobilized cells.

* * * * *